US011860095B2

(12) United States Patent
Frischauf et al.

(10) Patent No.: US 11,860,095 B2
(45) Date of Patent: Jan. 2, 2024

(54) METHOD AND SENSOR FOR DETECTING PRESENCE OR ABSENCE OF A CONTAMINANT

(71) Applicant: Radiometer Medical ApS, Brønshøj (DK)

(72) Inventors: Peter Frischauf, Brønshøj (DK); Michael Taagaard, Brønshøj (DK); Flemming Aas, Brønshøj (DK)

(73) Assignee: Radiometer Medical ApS, Brønshøj (DK)

( * ) Notice: Subject to any disclaimer, the term of this patent is extended or adjusted under 35 U.S.C. 154(b) by 16 days.

(21) Appl. No.: 17/649,564

(22) Filed: Feb. 1, 2022

(65) Prior Publication Data

US 2022/0187207 A1  Jun. 16, 2022

Related U.S. Application Data

(63) Continuation of application No. 16/955,183, filed as application No. PCT/EP2018/084526 on Dec. 12, 2018, now Pat. No. 11,268,905.

(30) Foreign Application Priority Data

Dec. 22, 2017  (DK) ........................... PA 2017 00741

(51) Int. Cl.
*G01N 21/64* (2006.01)
*G01N 33/49* (2006.01)

(52) U.S. Cl.
CPC ..... *G01N 21/6428* (2013.01); *G01N 21/6408* (2013.01); *G01N 33/49* (2013.01);
(Continued)

(58) Field of Classification Search
CPC . G01N 21/6428; G01N 21/6408; G01N 33/49
See application file for complete search history.

(56) References Cited

U.S. PATENT DOCUMENTS

| 5,030,420 A | 7/1991 | Bacon et al. |
| 8,354,015 B2 | 1/2013 | Kaltenbeck et al. |

(Continued)

FOREIGN PATENT DOCUMENTS

| EP | 2 738 544 A1 | 6/2014 |
| JP | 59-170748 A | 9/1984 |

(Continued)

OTHER PUBLICATIONS

International Search Report for International Application No. PCT/EP2018/084526, dated Mar. 19, 2019 (three pages).

(Continued)

*Primary Examiner* — Hugh Maupin
(74) *Attorney, Agent, or Firm* — FINNEGAN, HENDERSON, FARABOW, GARRETT & DUNNER, LLP

(57) ABSTRACT

The present invention relates in one aspect to a method of detecting a contaminant in a measurement chamber (201) of a sample analyzer (200). The sample analyzer (200) comprises an optical sensor with a sensor layer (205) comprising a luminophor (201), wherein the sensor layer (205) has a sensor surface (206) forming an interface to the measurement chamber (201). The method comprises steps of: filling the measurement chamber with a fluid sample; applying a stimulus to the luminophor in the sensor layer; detecting luminescence emitted from the luminophor in the sensor layer in response to the stimulus as a function of time; obtaining a time sequence of measurement values for the detected luminescence; based on the time sequence, determining an actual value of a first parameter and an actual value of a second parameter, wherein one of the first and second parameters is sensitive to a change in refractive index across the interface between the sensor layer and the measurement chamber, and wherein the other one of the first
(Continued)

and second parameters is not sensitive to said change in refractive index across the interface between the sensor layer and the measurement chamber; developing an expected value for the second parameter based on the actual value of the first parameter; comparing the expected value for the second parameter to the actual value of the second parameter; and determining the presence (or absence) of a contaminant based on the comparison. In a further aspect, a sample analyzer configured for detecting contaminants in the measurement chamber using embodiments of the above method is provided.

20 Claims, 6 Drawing Sheets

(52) U.S. Cl.
CPC .............. *G01N 2021/6432* (2013.01); *G01N 2021/6439* (2013.01); *G01N 2201/062* (2013.01); *G01N 2201/06113* (2013.01)

(56) References Cited

U.S. PATENT DOCUMENTS

| | | |
|---|---|---|
| 9,709,499 B1 | 7/2017 | Crafton et al. |
| 2003/0080002 A1 | 5/2003 | Taagaard et al. |
| 2006/0171845 A1 | 8/2006 | Martin |
| 2008/0266545 A1 | 10/2008 | Hansen |
| 2009/0199619 A1* | 8/2009 | Keller ............... B01D 67/0046 428/158 |
| 2009/0216097 A1* | 8/2009 | Wilson ............... A61B 5/1459 600/327 |
| 2010/0277727 A1 | 11/2010 | Schlaminger |
| 2011/0105869 A1* | 5/2011 | Wilson ............... A61B 5/14542 600/323 |
| 2012/0032095 A1 | 2/2012 | Nichols et al. |
| 2017/0226571 A1* | 8/2017 | Finkelstein .......... G01N 33/582 |
| 2019/0357825 A1 | 11/2019 | Chen |

FOREIGN PATENT DOCUMENTS

| | | |
|---|---|---|
| JP | 63-011135 A | 1/1988 |
| JP | 2003-513269 A | 4/2003 |
| JP | 2009-222429 | 10/2009 |
| JP | 2009-281794 A | 12/2009 |
| JP | 2010-525340 | 7/2010 |
| JP | 2011-185841 | 9/2011 |
| JP | 2012-523006 A | 9/2012 |
| WO | WO 89/09390 | 10/1989 |
| WO | WO 01/33195 A1 | 5/2001 |
| WO | WO 2017/108647 A1 | 6/2017 |

OTHER PUBLICATIONS

Written Opinion of the International Searching Authority for International Application No. PCT/EP2018/084526 (ten pages).

\* cited by examiner

METHOD AND SENSOR FOR DETECTING PRESENCE OR ABSENCE OF A CONTAMINANT

This application is a continuation of application Ser. No. 16/955,183, filed Jun. 18, 2020, which is a national stage filing under 35 U.S.C. § 371 of International Patent Application No. PCT/EP2018/084526, filed on Dec. 12, 2018, which claims priority to Danish Patent Application No. PA 2017 00741, filed on Dec. 22, 2017, the entire contents of each of which are incorporated herein by reference.

The present invention relates in one aspect to a method of detecting a contaminant in a measurement chamber of a sample analyzer, wherein the sample analyzer comprises an optical sensor with a sensor layer comprising a luminophor, wherein the sensor layer has a sensor surface forming an interface to the measurement chamber.

In a particular aspect, the present invention relates to a method of detecting a contaminant in a body fluid analyzer, such as a blood analyzer, the analyzer comprising an optical sensor configured for measuring a body fluid parameter, such as the partial pressure of oxygen in a blood sample, and to a body fluid analyzer, such as a blood analyzer, comprising a measurement chamber with such an optical sensor, and a signal processor, the analyzer being configured for detecting a contaminant in the measurement chamber.

According to a further aspect, the invention relates to an optical sensor for detecting a contaminant in the measurement chamber.

According to a yet further aspect, a computer-implemented method of detecting a contaminant in a sample analyzer, and a corresponding software product that can be loaded into a signal processor of a sample analyzer are provided. Also in this aspect, the sample analyzer may be a body fluid analyzer, such as a blood analyzer for analyzing e.g. a whole blood sample.

BACKGROUND OF THE INVENTION

Analyzers for measuring physical parameters of analytes in a liquid sample by means of respective analyte sensors are widely used in various industries, such as food industry, environmental industry, as well as medical and clinical industry. To ensure both accurate and precise results, the performance of such analyzers and the associated sensors is continuously scrutinized. This typically includes both detailed calibration and quality control procedures using standardized reference liquids including the respective analytes in well-defined compositions. The accurate and precise operation of analyzer systems is of particular importance in clinical analysis applications for analyzing physical parameters of analytes in bodily fluids, such as whole blood. In addition to the accuracy, precision, and reliability requirements, such analyzer systems for clinical applications are also subject to further critical constraints, such as a short time to obtaining a measurement result, and the capability of providing the highly reliable results from very small sample volumes.

The combination of all these constraints is particularly relevant in blood analyzers. Blood analyzers provide measurements of various parameters for analyzing the blood of a mammal subject, e.g. for establishing and/or monitoring a biological condition of the subject. Typically, the mammal subject is a human patient. In a variety of instances, it is desirable to measure e.g. the partial pressure of blood gasses in a whole blood sample of the mammal subject, concentrations of electrolytes and metabolites in the blood sample, as well as the hematocrit value of the blood sample. For example, measuring $pCO_2$, $pO_2$, pH, $Na^+$, $K^+$, $Ca^{2+}$, $Cl^-$, glucose, lactate, creatinine, urea and hemoglobin and hemoglobin-derivate values are primary clinical indications in assessing the condition of a medical patient. A number of different analyzers currently exist for making such measurements. Such analyzers are able to perform precise measurements in order to provide the most meaningful diagnostic information.

In order to use as little of the patient's blood as possible in each analysis performed, the measuring chamber, which is employed to analyze a blood sample, is preferably relatively small. Performing blood analysis using a small blood sample is important when a relatively large number of samples must be taken in a relatively short amount of time or if the volume of blood is limited, as in neonates. For example, patients in intensive care require a sampling frequency of 15-20 per day for blood gas and clinical chemistry measurements, leading to a potentially large loss of blood during patient assessment. Furthermore, in order to limit the number of tests which must be performed it is desirable to gather as much information as possible upon completion of each test. Furthermore, for the same reasons, it is important that the measurements and corresponding analysis results obtained from these measurements are reliable. Each measurement is therefore typically subject to a calibration and/or quality control procedure using different rinsing, calibration and/or reference liquids and the measurement chamber is thoroughly rinsed after each measurement to avoid contamination of any subsequent measurements.

However, a common issue in blood analyzers, in particular in systems with very small measurement chambers, is due to the presence of clots in whole blood samples. The clots may result in the formation of plugs impeding, obstructing or even completely blocking the fluid passages of the measurement chamber. Such clots may severely affect the measurements or even cause damage to the measurement chamber/sensor assembly. Known systems may therefore monitor the filling and discharge procedures for abnormalities in order to e.g. generate an alarm, stop the fluid handling infrastructure from feeding further fluid to the measurement chamber, and requesting a rinse and/or initiating an automated rinsing procedure. For example, the filling of the measurement chamber may be monitored by liquid sensors for detecting the passage of a liquid interface at an inlet upstream of the measurement and the corresponding subsequent occurrence of the liquid at an outlet downstream of the measurement chamber after an expected filling time. Unexpected behavior, e.g. expiry of the expected filling time without positive detection of the liquid interface at the outlet liquid sensor, may result in an alarm and/or initiation of a rinsing/maintenance procedure. Furthermore, by designing a simple flow path through the measurement chamber the formation of deposits can be counteracted and rinsing/washout can be facilitated.

While such strategies for detecting the presence of a clot in the measurement chamber are implemented and proof to be most helpful for a reliable operation of blood analyzer systems, it has been observed by the inventors that not all artifacts may be accounted for by these strategies and detection techniques. The inventors have indeed identified that further artifacts may arise due to clots, which are normally not detectable by the known clot detection routines that are based on e.g. flow behavior. Clots that do not noticeably affect the filling and discharge flow in the measurement chamber may nevertheless cause a severe distortion of the physical parameters of at least some of the analytes for a given sample, thus leading to erroneous analysis results. Therefore, there is a need for rapidly and reliably detecting any such additional causes of potential artifacts in blood analyzers in order to ensure accuracy and precision of the measurements and avoid the waste of valuable patient blood. Furthermore, such additional artifacts may also occur more generally in liquid sample analyzers. To address such additional causes of artifacts, the inventors have, in co-pending patent applications WO2017/108646A1 and WO2017/108647A1, which are hereby incorporated by reference, suggested different techniques for detecting clots by analyzing deviations of sensor response from an expected behavior. The clot detection disclosed in WO2017/108646A1 relates to a method based on an expected change i.e. a linear regression of the measurement results from at least two sensors, where deviation from the expected change is indicative of a clot. Clot detection in WO2017/108647A1 discloses a method in which a clot may be seen as a reservoir with a capacity for the uptake and emission of analyte, thereby causing pollution by acting as an analyte source or as an analyte sink whenever there is a gradient in the analyte concentration between the clot and the surrounding liquid sample.

However, further techniques for the detection of fouling or other contaminants in a measurement chamber of a liquid sample analyzer are still desired in order to further improve the reliability of the obtained measurement results, in particular when using very small sample volumes and/or when using samples with limited availability as already discussed above.

One type of analyte sensors are optical sensors with a sensor layer in contact with the measurement chamber. The sensor layer is sensitive to an amount of an analyte present in the fluid sample that is provided in the measurement chamber. The optical sensor further comprises instrumentation for the optical readout of the sensor layers' response to the presence of the analyte. The readout means typically comprise means for providing a stimulus to the sensor layer, optical elements, such as lenses and/or optical wave guiding components for collecting radiation emitted from the sensor layer in response to the stimulus, and further for transferring the collected luminescence radiation to detection means of the optical sensor. The stimulus is typically a radiation source, such as a laser or light emitting diode (LED), arranged and configured to provide optical probing radiation to the sensor layer. Optical sensors may, for example be of the fluorescence quenching type. The sensor layer of a luminescence quenching type sensor comprises a luminophor that is excited by the stimulus provided, such as excitation radiation guided to the sensor layer. The excited luminophor relaxes, amongst others, along radiative pathways, thereby emitting luminescence, which upon termination of the stimulus decays with a characteristic lifetime. The luminophor is selected such that the luminescence is quenched by the presence of the analyte acting as a so-called quenching agent. As a consequence, the characteristic lifetime of the luminescence emitted by the sensor layer depends on the amount of the analyte present in the sensor layer. An increase in concentration of the luminescence quenching analyte results in a decrease of the observed luminescence lifetime, whereas a decrease in concentration results in an increased lifetime. In order to provide proper results, the measurement is typically conducted at equilibrium conditions, i.e. the fluid sample is provided in the measurement chamber in such a manner that the concentration of the analyte in the sensor layer corresponds to the concentration in the sample, e.g. through diffusive exchange of analyte between the sensor layer and any fluids presented in the measurement chamber. The optical sensor may further comprise optional means for optically selecting and/or analyzing the radiation collected from the sensor layer, such as optical filters and/or optical amplifiers, before the light is received by the detection means. The detection means convert the detected luminescence radiation to a corresponding signal. The optical sensor is thus, configured to provide a signal representative of the amount of the analyte for which it is sensitized. The signal from the optical sensor is then typically provided to processing means in the sample analyzer for analog and/or digital signal processing, passed to further storage means for storage as measurement data, displayed and/or presented as analysis results at an output.

To give an example of a sensor, which, when used in a blood analyzer, is of particular importance for patient health and safety is the sensor determining the partial pressure of oxygen ($pO_2$). Such optical detectors for blood gas measurements, such as for $pO_2$-measurements, are for example known from U.S. Pat. No. 5,564,419A. The results obtained from $pO_2$-measurements can directly affect the treatment of the patient—particularly in emergency or intensive care situations. The $pO_2$ sensor may be an optical sensor with a sensor layer comprising a luminophor sensitive to the presence of oxygen in the sample. A contamination of the $pO_2$ sensor of a blood analyzer will affect the measurement and thus increase the risk for wrong treatment of the patient.

Accordingly, there is a further need for rapidly and reliably detecting any such additional causes of potential artifacts in sample analyzers in order to ensure accuracy and precision of the measurements. In particular, a rapid, if not immediate feedback on the reliability of measurements in sample analyzers, such as for measuring body fluid parameters, is desired in order to validate these measurements without delay.

Object of the present invention is therefore to provide a further method of detecting contamination in a measurement chamber with improved sensitivity and/or response time, and a system adapted to perform such detection method with improved sensitivity and/or response time. According to a further aspect, a further object is to provide a detection scheme allowing for an improved performance for the rapid and reliable detection of invalidating artifacts stemming from measurement chamber contamination.

SUMMARY OF THE INVENTION

A first aspect of the invention relates to a method of detecting a contaminant in a measurement chamber of a sample analyzer, wherein the sample analyzer comprises an optical sensor with a sensor layer comprising a luminophor, wherein the sensor layer has a sensor surface forming an interface to a fluid sample in the measurement chamber, the method comprising the steps of:
  filling the measurement chamber with a fluid sample;
  applying a stimulus to the luminophor in the sensor layer;
  detecting luminescence emitted from the luminophor in the sensor layer in response to the stimulus as a function of time;
  obtaining a time sequence of measurement values for the detected luminescence;
  based on the time sequence, determining an actual value of a first parameter and an actual value of a second parameter, wherein one of the first and second parameters is sensitive to a change in refractive index across the interface between the sensor layer and the measurement chamber, and wherein the other one of the first and second parameters is not sensitive to said change in refractive index across the interface between the sensor layer and the measurement chamber;

developing an expected value for the second parameter based on the actual value of the first parameter;

comparing the expected value for the second parameter to the actual value of the second parameter; and determining the presence of a contaminant or determining the absence of a contaminant, based on the comparison.

The sample space of the measurement chamber is filled so as to contact the sensor surface with the sample fluid, and with the purpose of performing a measurement on the fluid sample. It is an important merit of the present invention to recognize and address the significance of small contaminant amounts deposited on the surface of the sensor layer forming the interface of an optical sensor to the measurement chamber. The present method allows for detecting the presence of contaminants in the sample space of the measurement chamber. More particularly, the method is sensitive to the presence of contaminants on the sensor surface of the optical sensor and capable of providing immediate feedback on the contamination state of an optical sensor, and the adjacent sample space. Moreover, the contaminant detection is suited for quality monitoring purposes by continuously analyzing the time-resolved luminescence data and providing almost instantaneous feedback to the measurement system/user on the quality of the measurement and on the internal state of the sample analyzer used for analyzing the fluid sample.

The term 'contaminant' as used herein refers to any substance in a fluid sample that potentially may interfere with a measurement to be performed on the fluid sample. The term 'fluid' as used herein refers to both 'liquid' and 'gas'. Examples of contaminants may be droplet remainders of a previously measured liquid sample, precipitations on the measurement chamber walls, and/or bubbles occurring in a liquid sample e.g. due to an improper filling of the measurement chamber with a liquid sample, or the like. The present method is particularly useful in the context of a re-usable measurement chamber, i.e. a multi-use measurement chamber, which after single use, i.e. after performing a measurement cycle on a single fluid sample, is not discarded, but emptied, rinsed, and filled again with a new fluid sample. However, it is also conceivable to use the contamination detection method in the context of a single-use measurement chamber, which after a measurement cycle on a fluid sample is discarded, e.g. for ensuring cleanliness and/or proper filling of the single-use measurement chamber, before the actual measurement is performed.

The sensor layer is transparent and has a sensor surface forming a front side interface towards the sample space. The front side interface is in contact with the fluid sample. Optical probing is performed from the back side, i.e. from the side facing away from the sample space. A stimulus is given, typically in the form of excitation light that is directed to the sensor layer from the backside, so as to produce an excited fraction of the luminophor in the sensor layer. The excited luminophor molecules relax back to a ground state under the emission of luminescence light, which may also be observed from the back side. The optical sensor therefore further comprises instrumentation for detecting and registering luminescence emitted from the luminophor, and thus to observe the sensor layer response to the applied stimulus.

The parameter, which does not dependent on the change in refractive index across the interface between the sensor layer and the measurement chamber, may be referred to as an "intrinsic" parameter. An "intrinsic" parameter is thus representative of the "intrinsic" characteristics/properties of the relaxation process of the luminophor dye, which involves the radiative recombination at the origin of the detected luminescence radiation—essentially independent of the optical structure in which the luminophor is embedded, in particular invariant with respect to changes in the optical properties of the interface with the measurement chamber at the sensor surface.

The luminescence radiation is generated within the sensor layer. Radiation emitted in the direction towards the sample space is reflected at the optical interface between the transparent sensor layer and the sample space. The back reflected luminescence radiation therefore contributes to the radiation that is collected for detection. The reflection depends on the optical properties of the interface, which on one side is determined by the optical properties of the sensor layer and on the other side is determined by the optical properties of the substances in the sample space, in contact with the sensor surface. The back-reflected radiation therefore comprises information about the optical properties of any substances in contact with the sensor surface. The substances may thus be distinguished by their optical properties. More particularly, any contaminants and the fluid sample are thus distinguishable by any differences in refractive index.

The parameter, which does, at least partly, dependent on the change in refractive index across the interface between the sensor layer and the measurement chamber, may be referred to as an, at least partly, "extrinsic" parameter. The "extrinsic" parameter is thus sensitive to the part of the detected luminescence radiation that is sensitive to the optical characteristics of the structure in which the luminophor is embedded and from which it is collected. In particular, the extrinsic parameter is sensitive to changes in the optical properties of the interface between the sensor layer and the measurement chamber.

For determining the presence or absence of a contaminant on the sensor surface, actual values for the first and second parameters are obtained from a time sequence of optical probing measurements using the optical sensor. The first and second parameters are thus physically related through the luminescence from which they originate. One of the two may however, vary according to the contamination state, which influences the optical properties of the interface between the sensor layer and the sample space as described above. To facilitate distinction between different contamination states of the optical sensor surface, reference information is provided. Reference measurements on one or more reference fluids are prepared beforehand to establish a unique relation between the first and second parameter for each of the one or more reference fluids. Suitable reference fluids may be any liquid and/or gas samples with known optical characteristics, such as an aqueous solution with a known composition as commonly used in medical sample analyzers for QC or calibration purposes, air prepared to a predefined state, nitrogen, a noble gas, such as argon, or the like. The reference measurements are performed for one or more known contamination states. Typically, the reference measurements are performed with a clean sensor surface, i.e. in the absence of any contamination on the sensor surface, the surface thus only being in contact with the respective reference fluid. The reference measurements provide reference information that may be stored or in any other way made accessible to a processor for later use. The reference information may be consolidated and/or stored in any suitable form, for example tabulated, in a parametrized relation, and/or as one or more coefficients in an equation describing the relation between the first and second parameters for at least one known contamination state, which most preferably is the above-described clean state of the sensor in respect of at least one reference fluid. The sample analyzer is thus configured for developing an expected value for one of the first and second parameters based on actual values for the other one of the first and second parameters. The developed expected value is then compared to the actual value of the other one of the first and second parameters. In case the two values match as expected, the absence of contamination is determined. In case a mismatch between the expected value and the actual value of the other one of the first and second parameters is observed, a contamination of the sensor surface can be concluded.

Advantageously, according to some embodiments, the first parameter is the one that is not-dependent on the optical properties of the interface at the sensor surface ("intrinsic"), and the second parameter is the one that is dependent on said interface (at least partly "extrinsic"). Further advantageously, the expected value is determined based on the actual value of the intrinsic parameter. Thereby, it is achieved that the expected value of the second parameter calculated on the basis of the first, intrinsic parameter is less prone to artefacts stemming from the optical structure of the detection instrumentation.

Any suitable luminophor may be used, in combination with an optical probing technique that allows for determining a first parameter and a second parameter of the luminescence radiation emitted in response to a stimulus applied to the luminophor, wherein one of the first and second parameters depends on the optical properties of the sensor layer/sample interface, and the other one does not as required above.

The optical sensor is typically arranged for measuring a particular physical parameter for an analyte in a fluid sample present in the measurement chamber. For example, the optical sensor may be arranged in a sensor cassette comprising a measurement chamber with an inlet and an outlet, and multiple analyte sensors, said analyte sensors each being adapted to measure a respective parameter in respect of an analyte. The optical sensor used for the detection of contaminants may be one of the analyte sensors. However, it is also conceivable that the optical sensor is dedicated to the detection of contaminants only. Advantageously, the optical sensor is placed in the measurement chamber in such a way that the probability of detecting a contaminant is enhanced, e.g. at a location where contaminants are more likely to be detected, or at a location where contaminants tend to accumulate. Further advantageously, the optical sensor used for the detection of contaminants may be placed at the inlet. This has the advantage that any contaminant introduced into measurement chamber from the outside has to pass by the optical sensor. Furthermore, flow conditions around an inlet port may entail an enhanced probability of contaminants depositing on the measurement chamber sidewalls. By placing the optical sensor used for the detection of contaminants, the probability of capturing a contaminant may thus be enhanced as compared to other locations. Alternatively or in addition thereto, according to further considerations, an optical sensor to be used for the detection of contaminants may also be placed opposite/vis-à-vis/of another sensor, e.g. a sensor that for some reason cannot itself be used for the detection of contaminants, that is particularly sensitive to the presence of contaminants, and/or that has a tendency to attract contaminants. For example, an optical sensor for the detection of contaminants may be placed at a location in the measurement chamber that is opposite to a sensor for measuring $pCO_2$. According to yet further considerations, an optical sensor for the detection of contaminants, wherein the optical sensor is also an analyte sensor for measuring a parameter in respect of a specific analyte, may also be placed so as to optimize for the analyte measurement. In case there is a conflict between these considerations, the skilled person can determine a location as a compromise, or according to further preferences/priorities. Depending on the sensor type, optical probing may involve a luminophor in the transparent sensor layer that is sensitive to the analyte, for example a luminophor that may be probed for the presence of the analyte using known luminescence quenching techniques. Examples for luminescence quenching dyes are generally known in the art. For example, porphyrin compounds, such as aryl-substituted tetrabenzoporphyrin, palladium porphyrin (e.g. PdTPP, or PdTFPP) for detecting the presence of oxygen acting as a quenching agent for these porphyrin-compound based dyes. The present method for detecting contaminants has the advantage that it may probe the radiation response from the same luminophor that is also useful for probing for the analyte. The present method is therefore, in a synergistic way, particularly useful for detecting contaminants on the surface of a sensor that is adapted for measuring analytes by luminescence-probing techniques and contaminant detection may thus be easily implemented in such a luminescence probing set-up.

The method for detecting contaminants may be used at any time before, immediately before, during, and/or after a measurement is performed, in order to provide instant feedback on the contamination state of the sensor surface. In certain cases, the contamination state of the optical sensor may also reflect the general contamination state of the measurement chamber. Thereby, instant information on the quality and reliability of a measurement is available. The instant availability of the contamination state information also allows for immediately taking corrective measures, such as to clean the sensor surface, the measurement chamber as a whole, before a new measurement is performed, or in some cases to apply adequate corrections at a data analysis level. Acting immediately upon the occurrence of a contamination state avoids waste of valuable sample material, that otherwise would result from a belated, retroactive invalidation of the sample results. Immediate corrective action is also important for providing the correct care here and now, e.g. in emergency or intensive care, where the difference can be live saving.

The present invention is particularly useful for the detection of contaminants, such as clots or bubbles, in the measurement chamber of a medical sample analyzer, and further for verification of the presence of a suspected contamination or after conclusion of measures for the removal of a previously detected contamination. The detection result may be used as a part of self-control routines of the medical sample analyzer, or may be requested by a user or otherwise be triggered externally. The detection result may further trigger an alarm or error state of the medical sample analyzer, and may also be used to invoke a contaminant removal procedure and/or request external service, maintenance or replacement of a faulty measurement chamber if removal of the contamination proofs unsuccessful.

Further according to some embodiments of the method, the presence of a contaminant is determined if the difference between the actual value of the second parameter and the expected value for the second parameter is above a threshold, and/or wherein absence of a contaminant is determined if the difference between the actual value of the second parameter and the expected value for the second parameter is below the threshold. Thereby a more reliable distinction between the presence and absence of contaminants is achieved. Furthermore, a threshold can be set so as to discriminate between insignificant and significant contamination according to the significance of an observed mismatch between the developed expected value and the corresponding actual value for the validity of measurements to be performed using the optical sensor.

Further according to some embodiments of the method, the fluid sample is an aqueous liquid. When the fluid sample is an aqueous solution, the method is particularly useful for the detection of gas phase contaminants, such as bubbles. For example, the sample may be an aqueous solution or other water-based liquid, such as for medical parameter analysis, blood, urine, or related calibration/QC solutions, and the contaminant may be a bubble of gas adhering to the sensor surface. The large difference in refractive index between the gas bubble and the aqueous sample allows for a reliable detection of the contaminant indicating a deviant result using the method on an aqueous sample liquid. Advantageously, the method of detecting a bubble is performed during or in connection with the preparation/presentation of a liquid sample in the measurement chamber, wherein a bubble having a refractive index comparable to a gas sample can be detected by filling the measurement chamber with the liquid sample, and performing the optical bubble detection method as described herein. Thereby an indication for a proper filling of the measurement chamber can be verified. This is particularly an advantage, when the volume of the measurement chamber is in very small, such as in an elongate channel shaped chamber with dimensions in directions transverse with respect to a principal axis of the chamber in the mm and sub-millimeter range.

Further according to some embodiments of the method, the fluid sample is a liquid with a refractive index between 1.20 and 1.50, such as between 1.25 and 1.45, between 1.30 and 1.40, or about 1.20; 1.25; 1.30; 1.35; 1.40; 1,45; or 1.50. Advantageously, the fluid sample is a liquid with a refractive index between 1.20 and 1.30, between 1.25 and 1.35, between 1.30 and 1.40, between 1.35 and 1.45; or between 1.40 and 1.50. Refractive index values are for a given sample analyzer configuration in respect of the wave lengths of the luminescence radiation emitted by the luminophor in response to the stimulus, and are for temperature ranges at which measurements are typically performed. For example for body fluids, the temperature at which the measurements are to be performed is typically specified to a range corresponding to body temperature, such as between 35° C. and 39° C.; between 36° C. and 38° C.; between 35° C. and 38° C.; between 36° C. and 39° C.; or about 35° C.; 36° C.; 37° C.; 38° C. or 39° C.

When using the herein disclosed method on sample liquids with a refractive index within the above-specified ranges a clear distinction of the sample from a gaseous contaminant at the sensor surface, such as a gaseous contaminant with a refractive index well below 1.10; below 1.05; below 1.01; or about 1.00 is achieved.

Further according to some embodiments of the method, the fluid sample is a gas. Another type of contaminant than bubbles in a liquid may be deposits on the surface of the sensor surface, such as a remainder from a liquid sample from a previous measurement cycle, which may collectively be referred to as "clots". When the fluid sample is a gas, the method is particularly useful for the detection of such clots. Clots may include droplets, precipitations, and/or may have a gel-like consistence with a refractive index corresponding to that of liquids, such as aqueous liquids. Refractive index values in the above-mentioned ranges, such as above 1.10, above 1.20, between 1.20 and 1.50, or any of the ranges or values mentioned above with respect to liquid samples. Due to the difference in refractive index between such a clot and a gas sample, these clots can be reliably detected in a manner analogue to detecting bubbles of gas in a liquid sample.

Advantageously, the method of detecting a clot is performed during or in connection with a purging cycle. The purging or rinsing cycle is typically performed after a measurement has been concluded with the purpose to clean the measuring chamber and prepare the measurement chamber for a new measurement. A clot having a refractive index comparable to a liquid sample can be detected by filling the measurement chamber with a reference gas sample, such as an argon or nitrogen gas sample, and performing the optical clot detection method as described herein, prior to filling the measurement chamber with a liquid sample, such as a valuable patient sample. Thereby an additional check of the measurement chamber is achieved, which allows for instant feedback, and take immediate corrective action so as to avoid waste of valuable patient samples.

Further according to some embodiments of the method, the gas has a refractive index of below 1.10; below 1.05; below 1.01, or about 1.

Further according to some embodiments of the method, the refractive index of the sensor layer is at least 1.40; between 1.40 and 1.45; at least 1.45; between 1.45 and 1.50; at least 1.50; between 1.50 and 1.55; or at least 1.55. As mentioned above, the successful detection of a contaminant relies on distinguishing the contaminant and the fluid sample by their refractive index. Preferably, the refractive index of the sensor layer differs at least from the refractive index of the fluid sample. Most preferably, the refractive index of the sensor layer differs from the refractive indices for both the fluid sample and the contaminant. Thereby, a reliable detection of the contaminant is achieved.

A typical optical sensor for use in a medical sample analyzer may have a sensor layer with a matrix made of a polymer material, such as e.g. cellulose acetate, polyurethane, polycarbonate/silicone copolymer, or polyvinylchloride (PVC), in which the luminophor is embedded. Matrix materials for optical sensors are discussed in detail in the background section of the international patent application publication WO2001/004631, wherein further useful matrix materials are disclosed in the claims of WO2001/004631. WO2001/004631 is hereby enclosed by reference in its entirety. The host material essentially determines the refractive index, which in the case of polymer materials, such as PVC is typically about 1.50, such as in the range from 1.45 and up to including 1.55. Unless specified otherwise, refractive index values are for the relevant detection spectral range with respect to the luminescence radiation emitted by the luminophor in the visible part of the spectrum. In so far a temperature dependence of the refractive index has to be taken into account, the refractive index values refer to temperatures corresponding to typical temperatures for performing measurements as already discussed above.

Further according to some embodiments of the method, the step of applying a stimulus to the luminophor includes illuminating the sensor layer with light in an excitation spectral range adapted for exciting the luminophor. The stimulus is typically applied in a pulsed or modulated manner with stimulation periods where the stimulus is in an ON-state, separated by idle periods where the stimulus is in an OFF-state. This allows for observing time dependent luminescence response of the sensor layer to the stimulus, and more particularly, the pulse and/or step response, of the sensor layer to the stimulus. Typical light sources used for such optical stimulation may include pulse laser sources or modulated light sources using light emitting diodes (LED). Using laser pulses, very short excitation pulses may be achieved, which are typically short as compared to lifetime of the luminescence radiation from the luminophor. LED-based modulated light allow for a less complex, and less costly setup and have longer pulse duration.

Further according to some embodiments of the method, the step of obtaining a time sequence of measurement values includes measuring the luminescence intensity at a plurality of at least three points in time. A minimum of three points in time is required in order to be able to obtain sufficient independent measurements for determining the actual values for the first and second parameters independent of each other. For reasons of noise reduction, a larger number of measurements may advantageously be used for the time sequence in order to improve reliability of the obtained values. Good results are for example achieved by using between 5-200 points; 5-150 points; 5-100 points; 10-200 points; 10-150 points; 10-100 points; 20-200 points; 20-150 points; 20-100 points; 30-200 points; 30-150 points; 30-100 points; or at least 5 points, at least 10 points, at least 20 points, at least 30 points, at least 40 points, at least 50 points, or at least 60 points in time. An upper limit of the number of measurement points to be acquired at different times may be subject to an upper limit for the total time to be spent for the detection procedure. A useful upper limit may be up to 100 points, up to 150 points, or up to 200 points in time.

Further according to some embodiments of the method, the time sequence of measurement values is obtained for a time window after termination of the stimulus. For example, the time window may start immediately upon termination of the stimulus. According to some embodiments, the step of obtaining the time sequence of measurement values may be triggered by the termination of the stimulus. By obtaining the time sequence of measurement values after termination of the stimulus, a more simple subsequent analysis of the time-sequence is achieved. After termination of the stimulus, the intensity of the luminescence radiation decays. By starting the measurement immediately after termination the largest signal intensity is achieved, thereby reducing noise issues.

Further according to some embodiments of the method, the time sequence of measurement values is obtained for a time window during application of the stimulus. In principle, it is also conceivable to derive useful actual values for the first and second parameters as required by the invention from a time sequence during or including a time period when the stimulus is applied, as long as any effects of the presence of the stimulus on the luminescence by the detector means and the time dependence thereof, e.g. due to continued excitation and/or re-excitation of luminophor dye molecules by the incident stimulus, is taken into account in the subsequent analysis, for example when developing an expected value for the second parameter from the first parameter. Furthermore, any additional background radiation or any other artefacts that may result from the presence of the time-dependent stimulus that is scattered into the detection portion of the optical sensor will have to be accounted for. The effect of any such artefacts may, for example, be determined beforehand by measuring the characteristics of the sensor response in reference measurements, in the absence of any contamination. This embodiment is useful in combination with the use of a stimulus with a longer duration, such as when using an LED based illumination source.

Further according to some embodiments of the method, the first parameter is the lifetime $\tau$ of the luminescence, or a corresponding parameter. According to this embodiment, the first parameter is an "intrinsic" parameter, i.e. a parameter intrinsic to the molecular processes governing the relaxation of the excited state of the luminophor, such as the lifetime $\tau$ (tau) of the luminescence decay. The intrinsic parameter thus only depends on the intrinsic interactions occurring in the sensor layer and does not depend on extrinsic interactions, such as the optics of the interface between the sensor layer and the fluid sample. Determining the fluorescence lifetime $\tau$ from the intensity decay in a time-sequence of luminescence measurements is known and can be directly implemented in a signal processor of the optical detector. The fluorescence lifetime is therefore a simple and reliable implementation for the first parameter as an intrinsic parameter.

Further according to some embodiments of the method, the second parameter is the intensity of the luminescence at a given point in time, or a corresponding parameter. According to this embodiment, the second parameter is the luminescence radiation intensity emitted from the sensor layer and collected by the optical detector at a given point in time, e.g. after termination of the stimulus. The collected intensity is an at least partly "extrinsic" parameter, i.e. a parameter that is influenced by factors extrinsic to the recombination processes governing the relaxation of the excited state of the luminophor. Extrinsic factors may include the optical environment of the sensor layer, e.g. the optics of the interface between the sensor layer and the fluid sample. Keeping all other configuration parameters of the optical detection set-up the same, the extrinsic parameter, here the luminescence intensity that is collected by the detector, is therefore sensitive to changes in refractive index at the sensor surface.

Further according to some embodiments of the method, the luminophor in the sensor layer is a phosphor with a luminescence lifetime from 1 µs and up to including 1 s; and/or wherein the luminophor in the sensor layer is a phosphor with a luminescence lifetime of at least 10 µs, at least 20 µs, at least 30 µs; at least 40 µs; at least 50 µs; at least 60 µs; at least 70 µs; at least 80 µs; at least 90 µs; at least 100 µs; at least 150 µs; or at least 200 µs; and/or wherein the luminophor in the sensor layer is a phosphor with a luminescence lifetime up to and including 1 s; 100 ms; 10 ms; 1 ms; 500 µs; 300 µs; 150 µs; 30 µs; or 15 µs.

Advantageously according to some embodiments, the luminophor in the sensor layer is a phosphor with a luminescence lifetime from 10 µs and up to including 10 ms, from 10 µs and up to including 1 ms, from 10 µs and up to including 100 µs, from 20 µs and up to including 50 µs, from 20 µs and up to including 30 µs.

Advantageously according to some embodiments, the luminophor in the sensor layer is a phosphor with a luminescence lifetime of at least 10 µs, at least 20 µs, at least 30 µs; at least 40 µs; at least 50 µs; at least 60 µs; at least 70 µs; at least 80 µs; at least 90 µs; at least 100 µs; at least 150 µs; or at least 200 µs; and/or wherein the luminophor in the sensor layer is a phosphor with a luminescence lifetime up to and including 1 s; 100 ms; 10 ms; 1 ms; 500 µs; 300 µs; 150 µs; 30 µs; or 15 µs.

For the purpose of these embodiments, the lifetime of the luminophor emission is considered in the absence of luminescence quenching effects. For a luminophor adapted for luminescence quenching measurements in respect of a quenching agent (the specific analyte), the lifetime is considered in the absence of the quenching agent. Furthermore, the luminophor emission lifetime is considered under relevant measurement conditions in the context of the application of the contamination detection method, as easily determined by a skilled person. For example, in the case of medical analysis equipment, such as point-of-care or laboratory equipment, the relevant temperature is typically specified to a range corresponding to body temperature, such as between 35° C. and 39° C.; between 36° C. and 38° C.; between 35° C. and 38° C.; between 36° C. and 39° C.; or about 35° C.; 36° C.; 37° C.; 38° C. or 39° C.

Further according to some embodiments of the method, the step of filling the measurement chamber includes bringing the fluid sample in a diffusive equilibrium with the sensor layer, at least with respect to one analyte. Bringing the fluid sample into a diffusive equilibrium state may require a time delay as a part of the filling step. Thereby, artefacts arising from a non-equilibrium concentration distribution between the sample and the sensor layer, where the analyte is measured, may be avoided. Thereby, a simplified and reliable contaminant detection procedure is achieved.

Advantageously according to some embodiments of the method, the optical sensor is adapted to measure one or more analytes in a fluid sample so as to determine a corresponding parameter of the analyte, such as pH, concentrations of electrolytes, concentrations of metabolic factors or concentrations of enzymes. The fluid sample may be a biological sample, such as a body fluid, i.e. a physiological fluid.

Examples of biological samples may include both liquid and gas samples. Liquid samples may be selected from the group of blood, diluted or undiluted whole blood, serum, plasma, saliva, urine, cerebrospinal liquid, pleura, synovial liquid, ascites liquid, peritoneal liquid, amniotic liquid, milk, dialysis liquid samples, or the like, as well as any quality control materials and calibration solutions used in analyzer equipment for measuring any of these fluids. Gaseous samples may include respirator gas, expiratory air, or the like, as well as any quality control and calibration materials used in analyzer equipment for measuring any of these fluids. The sample may be treated prior to testing in order to make it more amenable to being tested. Pretreatment methods may include dilution, filtration, concentration, extraction, removal or inactivation of components which might interfere with the results, and addition of reagents. Examples of other biological samples include fermentation broths or microbial cultures, waste water, food products, and the like.

Examples of parameters in respect of analytes, which may be determined by means of the optical sensor of the invention include: $pO_2$, $pCO_2$, pH; concentrations of electrolytes such as $Li^+$, $Na^+$, $K^+$, $Ca^{2+}$, $Mg^{2+}$, $Cl^-$, $HCO^{3-}$ or $NH_3$ ($NH_4^+$); concentrations of metabolic factors, such as glucose, creatinine, urea (BUN), uric acid, lactic acid, pyruvic acid, ascorbic acid, phosphate or protein; concentrations of enzymes such as lactic acid dehydrogenase, lipase, amylase, choline, esterase, alkaline phosphatase, acid phosphatase, alanine amino transferase, aspartate, amino transferase, or creatinine kinase.

Further according to some embodiments of the method, the optical sensor is adapted for measuring a partial pressure of a gas fraction in the fluid sample, such as $pO_2$, or $pCO_2$.

Further according to some embodiments of the method, the sensor layer is adapted for the diffusive uptake of an analyte from the fluid sample, and the luminophor in the sensor layer is susceptible to luminescence quenching, due to the presence of the analyte in the sensor layer.

Thereby, the analyte measurement and the contaminant detection can be combined in a synergistic manner. Using luminescence quenching detection, a sensitive and precise method of determining concentrations of specific analytes acting as quenching agent for the luminophor in the sensor layer is provided. Advantageously, the luminescence quenching measurements may be evaluated using a Stern-Volmer-type analysis in a known manner. At the same time, using the present invention, the luminophor emission can be used for reliably detecting contamination on the sensor surface. The contamination detection can be achieved essentially instantly, thus allowing corrective measures to be taken immediately, such as compensating for artefacts resulting from any such contamination and/or attempting to remove the contaminant. As a consequence an enhanced precision of the optical sensor measurement is achieved.

Further according to some embodiments of the method, the optical sensor is adapted to determine a parameter of the fluid sample in respect of one or more analytes.

Further according to some embodiments of the method, the parameter of the fluid sample in respect of one or more analytes is selected from the group of: $pO_2$, $pCO_2$, pH; concentrations of electrolytes such as $Li^+$, $Na^+$, $K^+$, $Ca^{2+}$, $Mg^{2+}$, $Cl^-$, $HCO^{3-}$ or $NH_3$ ($NH_4^+$); concentrations of metabolic factors, such as glucose, creatinine, urea (BUN), uric acid, lactic acid, pyruvic acid, ascorbic acid, phosphate or protein; concentrations of enzymes such as lactic acid dehydrogenase, lipase, amylase, choline, esterase, alkaline phosphatase, acid phosphatase, alanine amino transferase, aspartate, amino transferase, or creatinine kinase.

Further according to some embodiments of the method, the fluid sample is a liquid, such as a body liquid, i.e. a physiological liquid. Correspondingly, a sample analyzer for use in performing the method is advantageously adapted to analyzing parameters of liquid samples, such as body liquids, i.e. physiological liquids. A medical sample analyzer may thus advantageously include a liquid handling system comprising valves, conduits, and/or pumping/transfer means, for controlling liquid flow, such as for filling and emptying of the measurement chamber with the liquid sample—preferably in an automated manner.

Further according to some embodiments of the method, the fluid sample is a liquid sample selected from the group of blood, diluted or undiluted whole blood, serum, plasma, saliva, urine, cerebrospinal liquid, pleura, synovial liquid, ascites liquid, peritoneal liquid, amniotic liquid, milk, dialysis liquid samples, or the like, as well as any quality control materials and calibration solutions used in analyzer equipment for measuring any of these fluids.

Further according to some embodiments of the method, the fluid sample is a gas, e.g. a medical gas, such as a physiological gas. Correspondingly, a sample analyzer for use in the method is advantageously adapted to analyzing parameters of medical gas samples. Examples of particularly useful medical gas samples are selected from the group of respirator gas, expiratory air, or the like, as well as any quality control and calibration materials used in analyzer equipment for measuring any of these fluids. A medical sample analyzer may thus advantageously include a gas handling system comprising valves, conduits, and/or pumping/transfer means, for controlling gas flow, such as for filling and emptying of the measurement chamber with the gas sample—preferably in an automated manner. Preferably, a medical sample analyzer comprises fluid handling means suited for both liquid and gas.

A second aspect of the invention relates to an optical sensor for the detection of a contaminant, the optical sensor comprising a sensor layer with a sensor surface forming an interface to a sample space, stimulus means, detection means, data storage means, and a signal processor, wherein the sensor layer comprises a luminophor adapted to emit luminescence radiation in response to an excitation stimulus applied to the luminophor; wherein the stimulus means is arranged for providing an excitation stimulus to the luminophor in the sensor layer; wherein the detection means is arranged to detect luminescence radiation emitted by the luminophor in response to the excitation stimulus; wherein the data storage means comprises programmed instructions for:

receiving a time sequence of measurement values for detected luminescence as signals from the optical sensor as an input;

determining an actual value of a first parameter and an actual value of a second parameter, based on the time sequence, wherein one of the first and second parameters is sensitive to a change in refractive index across the interface between the sensor layer and the sample space, and wherein the other one of the first and second parameters is not sensitive to said change in refractive index across the interface between the sensor layer and the sample space;

developing an expected value for the second parameter based on the actual value of the first parameter;

performing a comparison of the expected value for the second parameter to the actual value of the second parameter; and determining presence or absence of a contaminant based on the comparison;

and wherein the signal processor is operable to execute said programmed instructions so as to produce an output indicative of the presence or absence of a contaminant.

Thereby, a particularly compact and robust detection of contaminants on the sensor surface is achieved, wherein the contaminants are distinguishable from a fluid sample by their difference in refractive index as discussed above with respect to the method for detecting a contaminant on a sensor surface facing towards a sample space. Further advantages of the optical sensor for the detection of a contaminant and further advantageous embodiments are, in an analogue manner, also evident from the above discussion of the method of detecting contaminants and of additional features of the embodiments of the method disclosed herein. For example, the optical sensor is advantageously adapted to measure one or more analytes in a fluid sample so as to determine a corresponding parameter of the analyte, such as $pO_2$, $pCO_2$, pH, concentrations of electrolytes, concentrations of metabolic factors, or concentrations of enzymes, as mentioned above.

The optical sensor, and advantageous embodiments thereof with the additional features as disclosed in the context of the method, is particularly useful for use in a measurement chamber of a fluid sample analyzer, preferably a medical sample analyzer.

In a third aspect, a measurement chamber comprises an optical sensor according to any of the embodiments disclosed herein. The measurement chamber is preferably adapted for testing for, or measuring parameters of, one or more analytes in a fluid sample. The optical sensor is arranged such that the sensor surface faces into a sample space defined by the measurement chamber.

In a fourth aspect, a fluid sample analyzer is adapted for performing a method of contaminant detection according to any of the embodiments disclosed herein, the fluid sample analyzer comprising a measurement chamber with inlet and outlet ports for feeding and discharging a fluid sample to the measurement chamber and an optical sensor according to any of the embodiments disclosed herein, the optical sensor being arranged such that the sensor surface faces into a sample space defined by the measurement chamber.

Further according to a fifth aspect, a computer-implemented method of detecting a contaminant in a measurement chamber of a sample analyzer comprises an optical sensor with a sensor layer comprising a luminophor, wherein the sensor layer has a sensor surface forming an interface to the measurement chamber, the method comprising the steps of:

receiving a time sequence of measurement values representing luminescence intensities as a function of time as detected in response to a stimulus applied to the luminophor;

based on the time sequence, determining an actual value of a first parameter and an actual value of a second parameter, wherein one of the first and second parameters is sensitive to a change in refractive index across the interface between the sensor layer and the sample space, and wherein the other one of the first and second parameters is not sensitive to said change in refractive index across the interface between the sensor layer and the sample space;

developing an expected value for the second parameter based on the actual value of the first parameter;

comparing the expected value for the second parameter to the actual value of the second parameter; and determining the presence or absence of a contaminant based on the comparison.

Also in this aspect, further advantageous embodiments and any advantages originating from these are in an analogue manner based on the additional features as discussed above with respect to the optical sensor and the method of detecting a contaminant.

Further according to a sixth aspect, a software product that can be loaded to a processor, the processor being configured for communicating with an optical sensor comprising a sensor layer, the sensor layer comprising a sensor surface facing towards a sample space, the sensor layer comprising a luminophor, the processor being further configured for controlling stimulus means adapted for exciting the luminophor, the software product comprising instructions for:

(i) operating stimulus means to apply a stimulus to the luminophor in the sensor layer;

(ii) operating the optical sensor to detect luminescence emitted from the luminophor in the sensor layer in response to the stimulus as a function of time;

(iii) obtaining a time sequence of measurement values for the detected luminescence;

(iv) based on the time sequence, determining an actual value of a first parameter and an actual value of a second parameter, wherein one of the first and second parameters is sensitive to a change in refractive index across the interface between the sensor layer and the measurement chamber, and wherein the other one of the first and second parameters is not sensitive to said change in refractive index across the interface between the sensor layer and the measurement chamber;

(v) developing an expected value for the second parameter based on the actual value of the first parameter;

(vi) performing a comparison of the expected value for the second parameter to the actual value of the second parameter; and (vii) determining the presence or absence of a contaminant on the sensor surface based on the comparison.

Also in this aspect, further advantageous embodiments and any advantages originating from these are in an analogue manner based on the additional features as discussed above with respect to the optical sensor and the method of detecting a contaminant.

BRIEF DESCRIPTION OF THE DRAWINGS

Preferred embodiments of the invention will be described in more detail in connection with the appended drawings, which show in FIG. 1 a diagram of a blood analyzer according to one embodiment;

FIG. 3 schematically, a detail of the optical sensor of FIG. 2; and in

DETAILED DESCRIPTION

Figure 1:
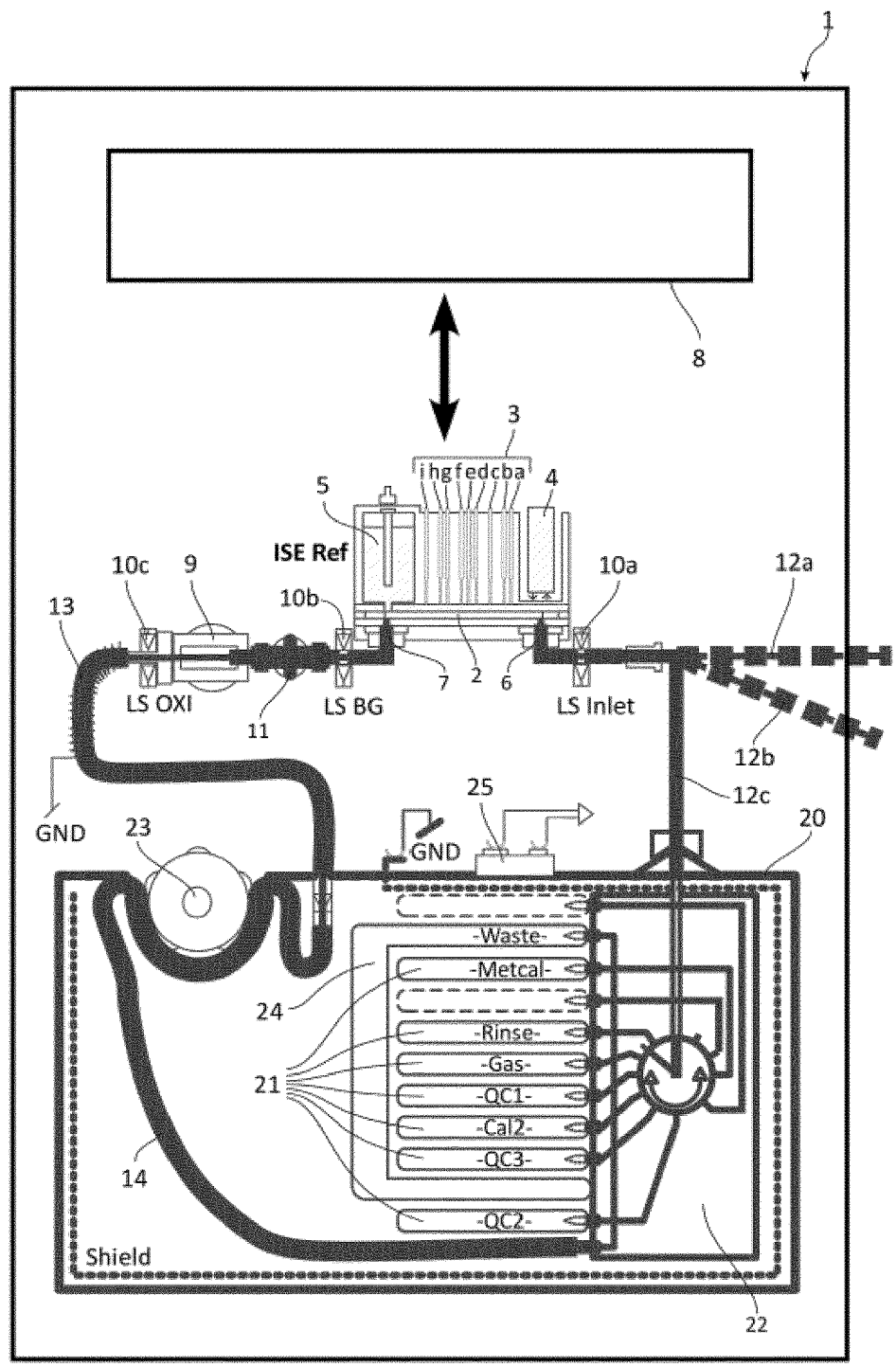

FIG. 1 shows schematically a liquid sample analyzer 1 with an analyzer part having a signal processor 8, one or more analyte sensors 3(a-i), 4, a measurement chamber 2, and fluid handling infrastructure 20. For performing measurements, the user may provide a liquid sample at an input port 12a/b of the analyzer 1. The liquid sample is transferred through an inlet port 6 to the measurement chamber 2 comprising a plurality of analyte sensors 3, 4. The analyte sensors 3, 4 are arranged to provide essentially simultaneous measurements on analyte parameters in a liquid sample, e.g. a whole blood sample. Preferably, the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in EP 2 147 307 B1. Following pre-programmed instructions loaded in a signal processor 8 and/or user input, measurements are performed using the analyte sensors 3, 4. The analyte sensors 3, 4 generate signals that are representative of a physical parameter for the respective analyte and provide the signals to the signal processor 8 of the analyzer part. The signal processor 8 is adapted to receive and process signals from the analyte sensors 3, 4, and present the processed signals as output to a user or to a subsequent/further data analysis. After measurement, the liquid sample is discharged, and the measurement chamber 2 is prepared for the next measurement. The embodiment of the analyzer shown in FIG. 1 is particularly adapted for the measurement of blood parameters, and further comprises an optional oxygenation measurement device 9 downstream of the measurement chamber 2. Performing the measurements, calibration tasks, and quality control procedures thus typically involves the loading, unloading, rinsing, cleaning and reloading of different liquids, which may be done by the fluid handling infrastructure 20. The fluid handling may be controlled in an automated way by the signal processor 8 according to pre-programmed instructions and/or user input. The fluid handling infrastructure 20 includes a number of reservoirs 21 pre-filled with process liquids (RINSE/CAL1, CAL2, QC1, QC2, QC3) for rinsing/wash-out, calibration and quality control tasks. The process liquids (RINSE/CAL1, CAL2, QC1, QC2, QC3) have a known composition. The exact composition of a given batch may be stored in a chip 25 that may be attached to a cassette comprising the reservoirs 21, wherein the chip 25 may be read by the signal processor 8. The process liquid (RINSE/CAL1, CAL2, QC1, QC2, QC3) for a given process step may be selected by a fluid selector valve 22, and via feed line 12c transferred through the inlet port 6 to the measurement chamber 2. Correct filling of the measurement chamber 2 may be monitored and verified by visual inspection or according to known procedures by observing the propagation of a liquid interface through the system by means of liquid sensors 10a, 10b, 10c located upstream and downstream of the measurement chamber, such as at the inlet 6 ("LS inlet" 10a), at the outlet 7 ("LS BG" 10b), and just after the oxygenation measurement device 9 ("LS OXI" 10c), respectively. The fluid flow through the analyzer is driven by a pump 23, here a peristaltic hose-pump arranged downstream of the measurement chamber 2 and the oxygenation measurement device 9 and connected thereto via fluid line 13. The discharged fluids are finally transported through fluid line 14 to the waste reservoir 24.

Upon start-up and, in an ongoing manner, during uptime, the analyzer 1 performs self-control routines. If any abnormality is detected, the analyzer 1 indicates the deviation to a user, and may further indicate ways of overcoming an error state. On the other hand, when the analyzer indicates normal operation, measurements can be performed immediately. Advantageously according to some embodiments, the self-control routines may be performed during idle times, i.e. when the analyzer is in an idle state, where it is not used for performing actual measurements on a user's sample. The self-control routines may include continued repetitive measurements performed on a calibration-grade process liquid with a precisely known composition, as e.g. stored on chip 25. The signals obtained for each of the different analyte sensors 3, 4 on the well-known composition may then be used to continuously update the reference for the respective analyte measurements.

Figure 2:
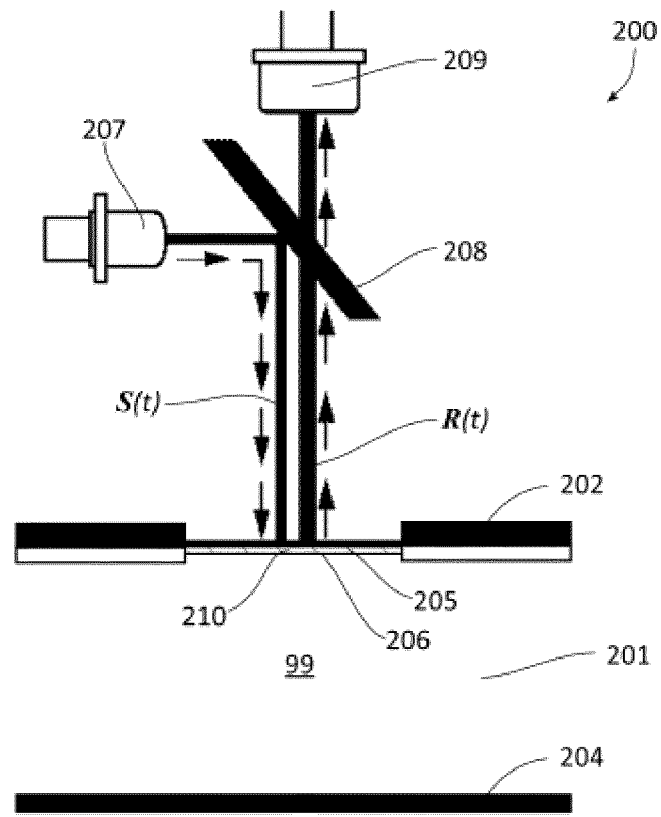
FIG. 2 schematically, an optical sensor according to one embodiment.
Figure 3:
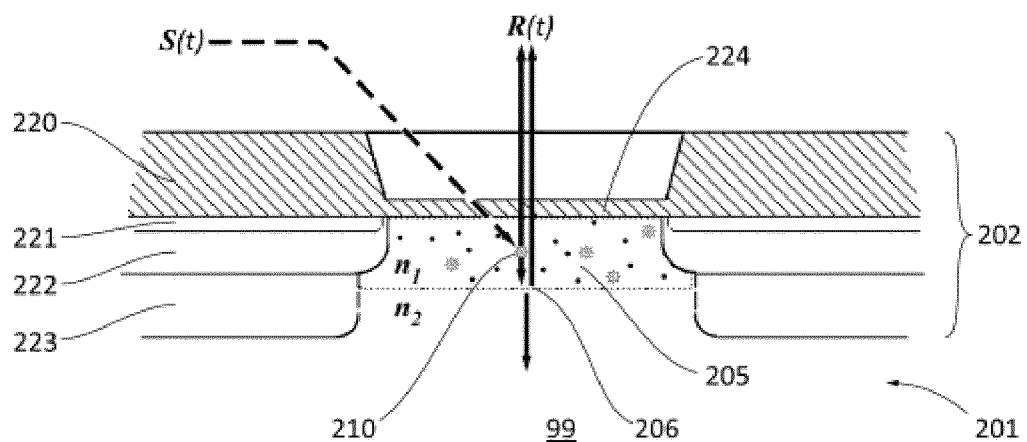

Turning to FIG. 2 and FIG. 3, an embodiment of an optical detector set-up is now discussed. FIG. 2 shows schematically an optical detector 200 according to one embodiment in contact with a measurement chamber 201 defined by sidewalls 202, 204. The optical detector 200 is adapted for measuring a physical parameter of an analyte in a fluid sample 99 placed in the measurement chamber 201, such as a partial pressure of an analyte-gas. The optical detector 200 has a sensor layer 205 with a sensor surface 206 facing towards the inside of the measurement chamber 201. The sensor surface 206 thus forms an interface to the measurement chamber 201 receiving the fluid sample 99, wherein the sensor surface 206 is adapted for directly contacting the fluid sample 99. The arrangement of the sensor layer 205 in the wall 202 of the measurement 201 is best seen in FIG. 3, which shows a detail of the part of the optical detector 200 that is integrated in the wall 202. In this particular embodiment, the wall 202 is made of a substrate 220, made e.g. of ceramics, carrying encapsulant and polymer layers 221, 222, 223. A thinned portion 224 of the substrate 220 allows for optical access to the sensor layer 205. The sensor layer 205 is applied to the front side of the substrate 220, i.e. to the side facing towards the measurement chamber 201, within an opening in the encapsulant and polymer layers 221, 222, 223 that is also aligned with the thinned portion 224. In this arrangement, the sensor layer 205 response can be probed optically from the backside of the substrate 220, i.e. from the side facing away from the measurement chamber 201, through the thinned portion 224 functioning as a window like optical access. Note that for reasons of clarity, the layer thicknesses shown in FIG. 3 are not to scale. Suitable thicknesses for a window portion 224 may be chosen, e.g. according to considerations of mechanical strength and optical transparency. Suitable thicknesses for a sensor layer 205 may be chosen, e.g. according to considerations of response time and of establishing an equilibrium state of the sensor layer 205 during measurements within a desired time frame, such as within 1 s, within 3 s, within 10 s, within 30 s, or within 1 min. These considerations may take into account, for example, the diffusivity of the relevant analyte into and out of the sensor layer 205. For example, the window portion 224 of the ceramic substrate 220 may have a thickness of about 100 µm, whereas a typical layer thickness of the sensor layer 205 may be in the range between 1 µm and 10 µm, typically between 1 µm and 4 µm, or about 2.5 µm.

The sensor layer 205 comprises a luminophor 210, i.e. a material emitting luminescence I(t) in response to an excitation-stimulus S(t). The excitation stimulus S(t) is typically provided in the form of pulsed or modulated light generated by a suitable light source 207, such as a light source using a light emitting diode or a laser, in an excitation wavelength range adapted to optically excite the luminophor 210 into an excited state from which it then decays under emission of radiation in an emission wave length range that is spectrally distinguishable from the excitation wavelength range. In the embodiment shown in FIG. 2, excitation light S(t) from an LED 207 is coupled by a mirror 208 at normal incidence onto the back side of the substrate 220, thus illuminating the sensor layer 205 through the thinned portion 224. The incident excitation light S(t) excites a fraction of the luminophor molecules 210 in the sensor layer 205, which responds by emitting luminescence light in essentially all directions, as indicated by the star symbols in FIG. 3. Typically, the luminophor is of the down-conversion type, i.e. the luminophor emission light is found at lower photon energies, or longer wavelengths, as compared to the excitation light. However, up-converting luminophor substances, i.e. substances where the luminophor emission light is found at higher photon energies, or shorter wavelengths, as compared to the excitation light, are also conceivable as long as the response radiation R(t) is spectrally distinguishable from the stimulus radiation S(t). Light emitted from the luminophor 210 is collected from the back side of the substrate 220, through the thinned portion 224 as response radiation R(t). The response radiation R(t) is then separated from the stimulus radiation S(t) by adequate spectral separation means, such as by means of a dichroic mirror 208. The response radiation R(t) is then detected by a photodetector 209, which generates a sensor output signal that can be amplified, acquired and processed in any suitable way by any suitable analog and/or digital data processing means as known in the art of sensor signal processing and data acquisition.

The intensity of the response radiation R(t) that is collected and detected by the detector 209 depends on the optical properties of the specific detection set-up, and in particular on the optical elements on the optical path from the luminophor 210 in the sensor layer 205 to the photodetector 209. Due to this dependence on factors extrinsic to the luminescence process, the collected and detected intensity of the response radiation R(t) may be called an "extrinsic" parameter. For example, the intensity of the collected response radiation R(t) depends on the difference in refractive index across the interface 206 between the sensor layer 205 having refractive index $n_1$ and the fluid sample having refractive index $n_2$ as best seen in FIG. 3. A luminophor molecule 210 that is excited by incident stimulus radiation S(t) emits luminescence in all directions. Luminescence light travelling in a direction away from the substrate 220 towards the fluid sample 99 is partly reflected at the interface 206 and partly transmitted into the fluid sample 99. The reflected part contributes to the collected and detected intensity of the response radiation R(t), whereas the transmitted part of the luminescence intensity is lost for detection. The effect of the interface 206 on the collection efficiency depends on the difference in refractive index between the sensor layer 205 ($n_1$) and the adjacent fluid sample 99 ($n_2$). As a consequence, the intensity of the collected and detected radiation R(t) is sensitive to changes in the refractive index $n_2$ of the fluid sample 99 in contact with the sensor surface 206. Keeping remaining configuration parameters of the optical detector set-up 200 comparable to each other, the intensity of the collected and detected radiation originating from the luminophor 210 in the sensor layer 205 can thus be used to discriminate between different sample substances that are distinguishable by their refractive indices, when these are in contact with the sensor surface 206. For example, the optical detector set-up 200 may be used to distinguish between a fluid sample 99 of an aqueous solution having a refractive index of about 1.3 and a fluid sample 99 of a gas having a refractive index of 1, wherein the sensor layer 205 includes e.g. a polymer matrix material hosting the luminophor 210, the matrix material having e.g. a refractive index of 1.5.

For a given optical detector set-up, the change in intensity to be expected from a given change in the refractive index of the fluid sample 99 may be determined empirically by routine experimentation. By way of example, for an optical detector setup 200 as described above, the ratio R(liquid)/R(gas) of the collected and detected intensities $R_{gas}(t)$ and $R_{liquid}(t)$ for a gas sample and for an aqueous solution presented at the interface 206, respectively, is determined as R(liquid)/R(air)=0.52. Since the luminophor employed is typically also sensitive to the presence of a specific analyte, here for example for measuring the partial pressure of oxygen $pO_2$ in the fluid sample 99, care has been taken to determine the ratio R(liquid)/R(gas) for comparable gas and liquid samples, i.e. gas and liquid samples with the same concentration of the specific analyte. For example, in the case of a gas analyte, such as oxygen, a gas sample with a specific partial pressure for that gas analyte may be selected as the gas sample, and a corresponding liquid sample of an aqueous solution with the same partial pressure of the gas analyte can be prepared by aerating the aqueous solution with gas of the same composition (e.g. using gas from the same source) as the gas sample until an equilibrium concentration is established. In so far the ratio of the intensities for R(liquid)/R(gas) is taken for comparable liquid and gas samples at a given point in time, the ratio is observed to be independent of the analyte concentration, which supports the extrinsic nature of the response radiation intensity as a parameter derivable from the collected and detected luminescence response.

The stimulus radiation S(t) is typically provided in one or more pulses. Typically, a sequence of pulses is provided, wherein the pulses are separated by idle periods where the stimulus is switched off. For a light source using LED emitters, the stimulus radiation is typically modulated in time as a sequence of ON-states separated by OFF-states, which may be considered as pulses and idle periods, respectively. After termination of the stimulus S(t), e.g. when switching from an ON-state to an OFF-state, the intensity of the luminescence I(t) decreases with a time constant that is characteristic for the luminophor, also referred to as the lifetime $\tau_0$. The observed lifetime $\tau_0$ is intrinsic to the recombination processes occurring in the luminophor. The lifetime $\tau_0$, as such, is therefore not affected by the particular configuration of the optical path of the emitted light from the luminophor to the detector, such as the presence of interfaces between optical elements (e.g. layers), or the refractive index or optical density of such optical elements (e.g. layers). The lifetime $\tau_0$ may therefore be referred to as an "intrinsic" parameter, which is derivable from the collected and detected luminescence response R(t).

For a given set-up for the optical detection, fluid samples with the same analyte concentration will yield the same result for the lifetime $\tau$. If the samples also have the same refractive index, the same intensity signal is expected at a given point in time after termination of the stimulus radiation.

In order for the optical detector 200 to function as a sensor for a specific analyte, the luminophor 210 is sensitive to the presence of the specific analyte, wherein the luminescence R(t) as collected and detected in response to the stimulus S(t) is a function of the concentration of the analyte in the fluid sample 99 in contact with the sensor surface 206. The optical detector is operated to generate a corresponding output signal, which can be analyzed to provide a measure for the concentration of the analyte. The underlying sensor principle may be for example the quenching of the luminescence emission from the excited luminophor by the presence of the analyte acting as a so-called quenching agent. As a consequence of the quenching mechanism, the lifetime $\tau_0$ and the intensity of the luminescence at a given point in time is a function of the analyte concentration.

Typically, the luminophors employed are phosphors with a lifetime $\tau_0$ above 1 µs in order to facilitate an easy detection of the time-dependence of the emitted luminescence R(t) with relatively simple instrumentation. For example, the luminophor may be a palladiumporphyrin, e.g. palladium(II)-tetraphenylporphyrin (PdTPP) or palladium (II)-tetra-(pentafluorophenyl)-porphyrin (PdTFPP), or any other suitable luminophor. Palladiumporphyrins are, for example, well suited for blood measurements when immobilized in a polymer matrix to form a sensor layer 205.

The analyte concentration of a fluid sample, such as the partial pressure of oxygen $pO_2$, may be determined from the observed decrease in lifetime due to luminescence quenching using the Stern-Volmer equation:

$$pO_2(\tau) = k * \left(\frac{\tau_0}{\tau} - 1\right),$$

wherein $\tau_0$ is the lifetime of the luminescence response R(t) for a sample with zero concentration, e.g. an argon gas sample. The sensitivity coefficient k may be determined from measurements on one or more samples with known analyte concentrations, for example an atmospheric air sample with 21% of oxygen at normal conditions/corrected for barometric pressure, or a calibration liquid (aqueous solution) that has been prepared with a predefined partial pressure of $O_2$, e.g. in the range between 50-250 mmHg, or a corresponding gas sample prepared with the same partial pressure of $O_2$.

Figure 4:
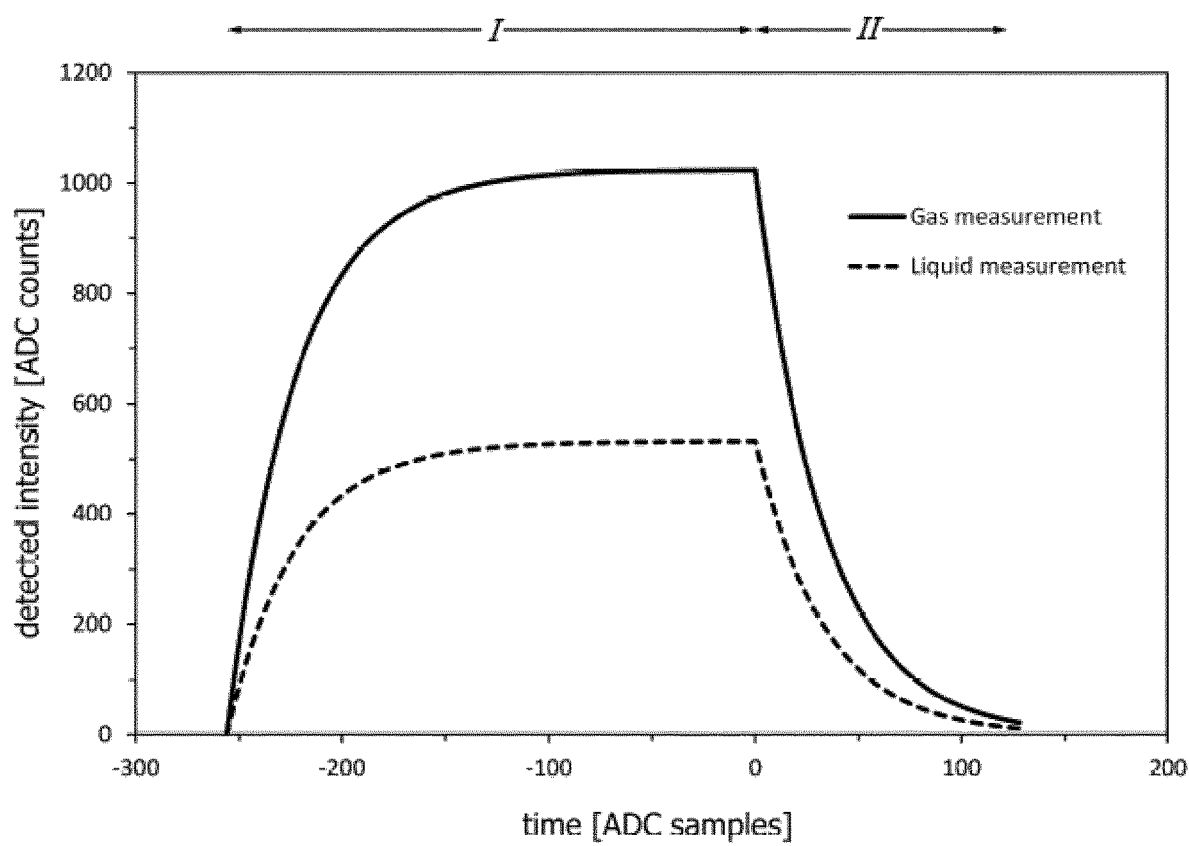
FIG. 4 a graph with the time-dependence of the luminescence intensity for two different sample fluids as detected with an optical sensor according to one embodiment.

FIG. 4 shows a graph with the time-dependence of the luminescence intensity for two different fluid samples as detected with an optical sensor according to one embodiment, namely for a gas sample and a liquid sample, respectively. The graph shows a plot of the luminescence intensity on the coordinate axis vs. time on the ordinate axis. The plot has a first, excitation phase "I", during which a stimulus radiation is in an ON-state, and a second, idle phase "II", during which the stimulus radiation is in an OFF-state. The first phase starts just before the ordinate value "−250", when the stimulus radiation is switched on, and terminates at the ordinate value "0", when the stimulus radiation is switched off again. The stimulus radiation pulse of phase "I" causes the luminescence emission to increase as a larger and larger fraction of the luminophor in the sensor layer is excited by the incident stimulus and subsequently relaxes through radiative processes. The increase in luminescence intensity tends to saturate as the excitation processes and the relaxation processes compete with each other. The second phase starts at the ordinate value "0", upon termination of the first phase. The second phase extends as long as the stimulus remains in the OFF-state, typically until the next excitation pulse starts. Upon termination of the stimulus radiation pulse, the luminescence intensity decreases as the fraction of excited luminophor decreases due to relaxation. The decrease is characterized by a lifetime $\tau$, which depends on the concentration of analyte in the two fluid samples.

Since both fluid samples have been prepared with the same analyte concentration and measurements, an analysis of the time dependence in the second phase of the plot yields the same characteristic lifetime for both samples. The difference in the observed intensity is a consequence of the difference in refractive index between the two samples, which are about 1.3 for the liquid sample and about 1 for the gas sample, wherein the sensor layer has a refractive index of about 1.5.

The optical detector used in the example is for measuring partial pressure of oxygen $pO_2$ in the fluid samples using an analyzer as described above with respect to FIG. 1. The gas sample of FIG. 4 is a reference gas that has been prepared with an oxygen-content at a partial pressure of approximately 500 mmHg and the liquid sample of FIG. 4 is an aqueous solution that has been aerated to an equilibrium state with a gas of the identical composition as the gas sample. The two measured sample fluids, gas and liquid, are thus prepared with the same partial pressure of oxygen $pO_2$ contained therein. The two gas and liquid samples are therefore at least comparable with respect to the analyte to which the optical detector is sensitive (here: oxygen).

Figure 5:
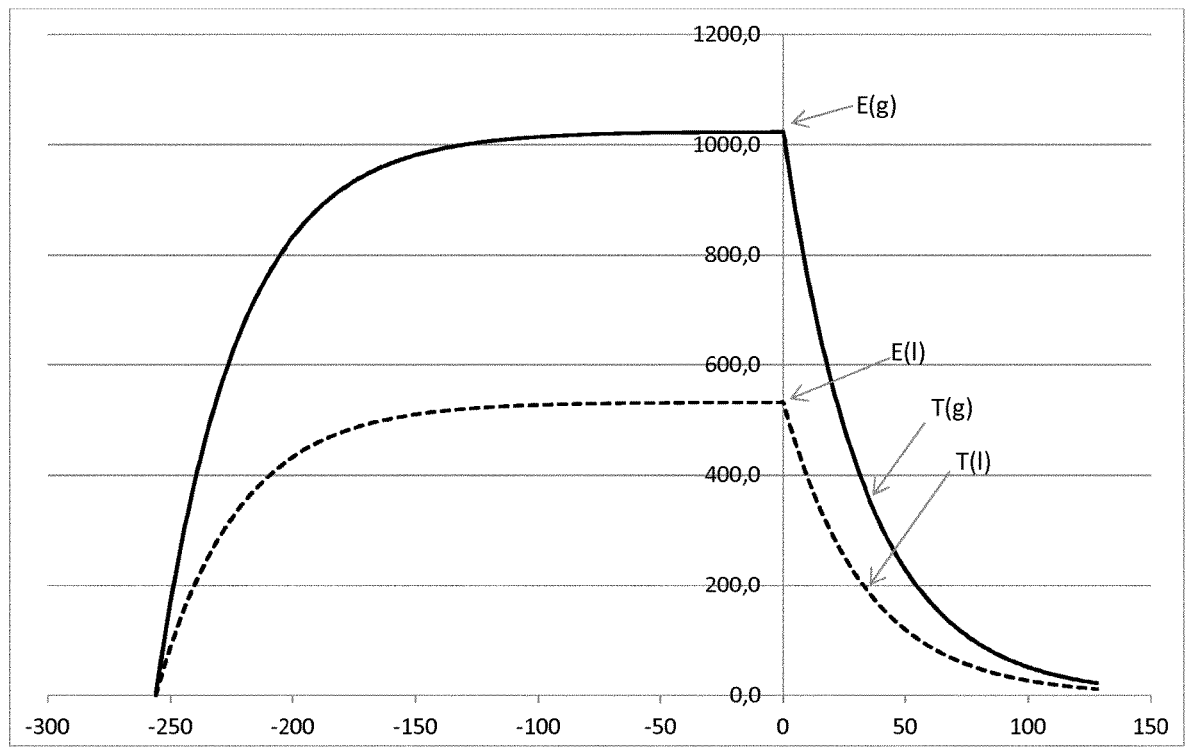
FIG. 5 shows the principle of bubble and clot check.

FIG. 5 shows the principle of bubble and clot check by pO2 measurement. The solid line is the calibration on a known gas (i.e. a reference gas) from where Energy gas, E(g) and tau gas, T(g) are determined. The dotted line is measurement on a liquid sample from where Energy liquid, E(l) and tau liquid, T(l) are determined. Data presented in the graph are pO2 measurement at the same pO2 level, i.e. with the same level of tau.

Bubble Check: BubbleFactor=Energy liquid/Tau liquid/ (Energy gas/Tau gas)

Nominal value liquid=LiquidFactor

LiquidFactor=Energy liquid/Energy gas=0.52 is empirically determined on the overall pO2 system and applies to all levels of pO2.

Clot Check: ClotFactor=Energy gas/Tau gas/(Energy gas/Tau gas)

Nominal value gas=1

The nominal value is the mean value which has been observed for a fluid sample without the presence of a bubble or clot. It is used for calculating the threshold, i.e. the upper and lower acceptance limits.

EXAMPLE 1

Figure 6A:
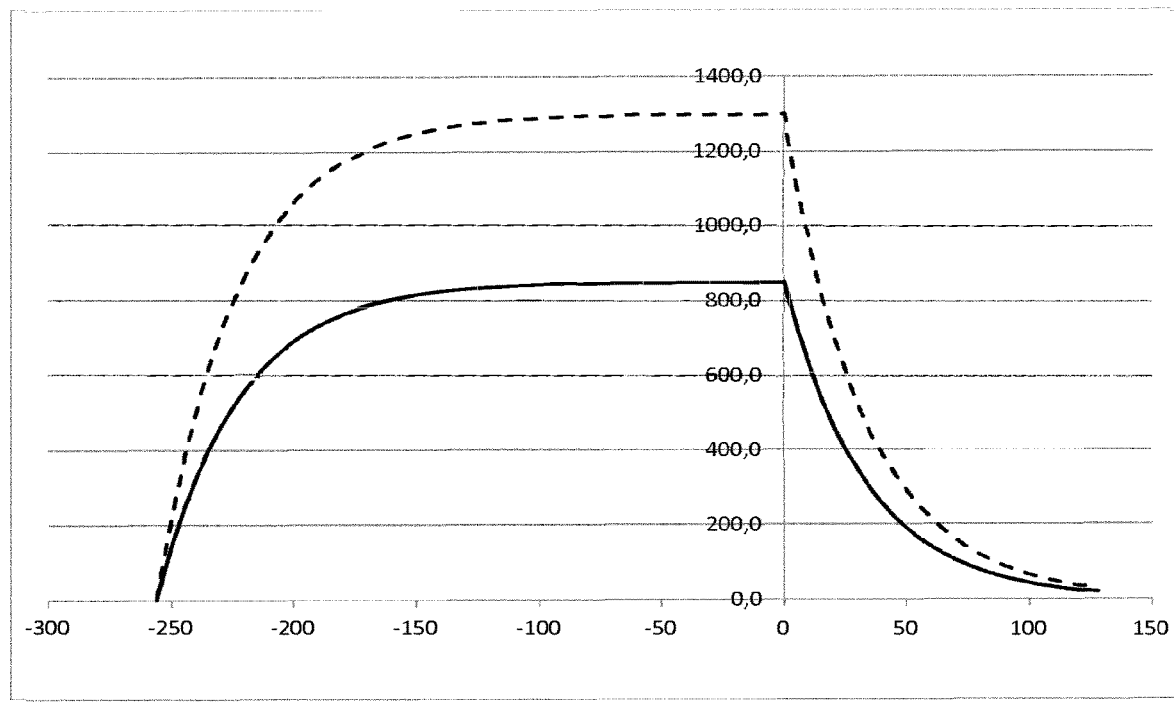
FIG. 6a shows the result from pO2 measurement on liquid samples without and with an air bubble.
Figure 6B:
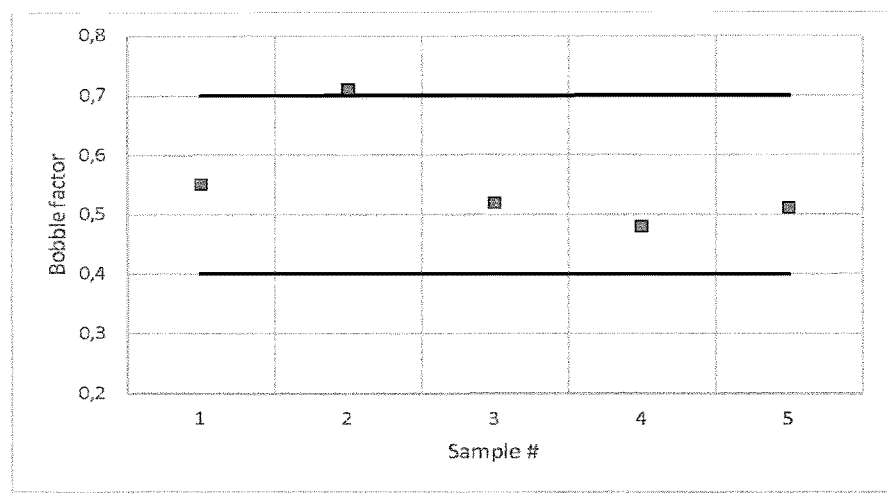
FIG. 6b shows the bubble factor for five samples of which four (sample 1, 3, 4, and 5) do not have a bubble and one (sample 2) has a bubble.

The result from pO2 measurement on Liquid samples without and with an air bubble is shown in FIGS. 6a & 6b. FIG. 6a shows the intensity over time for a sample without (solid line) and with (dotted line) a bubble. FIG. 6b shows the bubble factor for five samples of which four (sample 1, 3, 4, and 5) do not have a bubble and one (sample 2) has a bubble.

TABLE 1

Calibration of the sensor and calculation of bubble factor for sample 2 & 3.

| Calibration of the sensor on gas with a level of 140 mmHg | | |
|---|---|---|
| E (g) | 1024 | count |
| T (g) | 2.50E−04 | microsec |
| Calculation of bubble factor on a sample with a bubble with a level of 70 mmHg (sample 2) | | |
| E (l) | 1300 | count |
| T (l) | 4.00E−04 | microsec |
| Calculation of bubble factor on a sample without bubble with a level of 70 mmHg (sample 3) | | |
| E (l) | 850 | count |
| T (l) | 4.00E−04 | microsec |

EXAMPLE 2

Figure 7A:
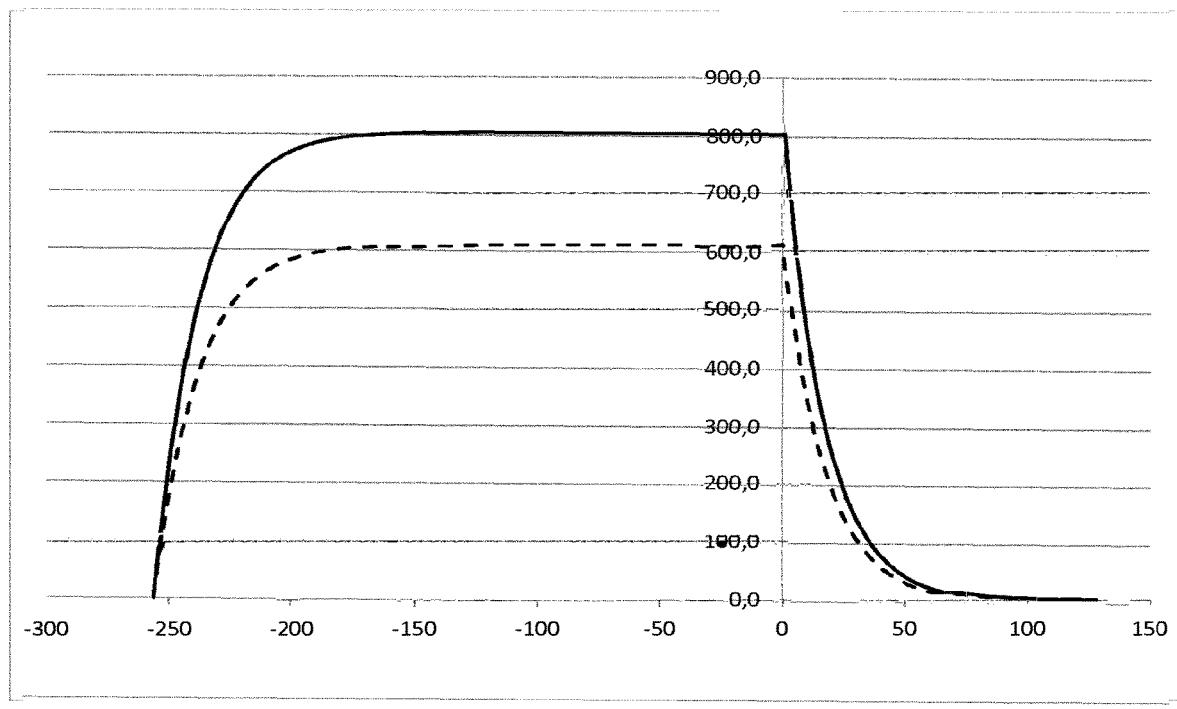
FIG. 7a shows the result from pO2 measurement on gas samples without and with a clot.
Figure 7B:
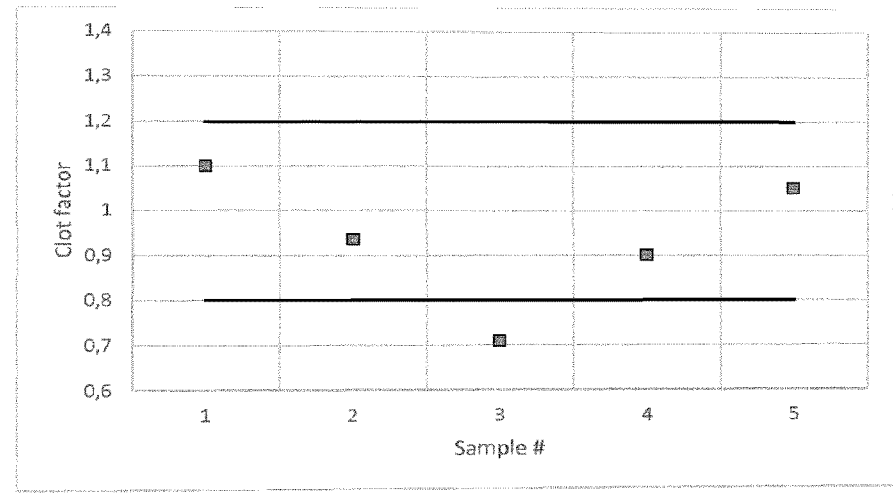
FIG. 7b shows the clot factor for five samples of which four (sample 1, 2, 4, and 5) do not have a clot and one (sample 3) has a clot.

The result from pO2 measurement on gas samples without and with a clot is shown in FIGS. 7a & 7b. FIG. 7a shows the intensity over time for a sample without (solid line) and with (dotted line) a clot. FIG. 7b shows the clot factor for five samples of which four (sample 1, 2, 4, and 5) do not have a clot and one (sample 3) has a clot.

TABLE 2

Calibration of the sensor and calculation of clot factor for sample 2 & 3.

| Calibration of the sensor on gas with a level of 140 mmHg | | |
|---|---|---|
| E (g) | 1024 | count |
| T (g) | 2.50E−04 | microsec |
| Calculation of clot factor for a sample without a clot with a level of 175 mmHg (sample 2) | | |
| E (g) | 805 | count |
| T (g) | 2.10E−04 | microsec |
| Calculation of clot factor for a sample with a clot with a level of 175 mmHg (sample 3) | | |
| E (g) | 610 | count |
| T (g) | 2.10E−04 | microsec |

The invention claimed is:

1. A method of detecting a contaminant in a measurement chamber of a sample analyzer, wherein the sample analyzer comprises an optical sensor with a sensor layer comprising a luminophor, wherein the sensor layer has a sensor surface forming an interface to a fluid sample present in the measurement chamber, the method comprising:

filling the measurement chamber with the fluid sample;

applying a stimulus to the luminophor in the sensor layer;

detecting luminescence emitted from the luminophor in the sensor layer in response to the stimulus as a function of time;

obtaining a time sequence of measurement values for the detected luminescence;

based on the time sequence, determining an actual value of a first parameter and an actual value of a second parameter, wherein one of the first and second parameters is sensitive to a change in refractive index across the interface between the sensor layer and the measurement chamber, and wherein the other one of the first and second parameters is not sensitive to said change in refractive index across the interface between the sensor layer and the measurement chamber; and providing feedback on a contamination state based on the actual value of the first parameter and the actual value of the second parameter.

2. The method according to claim 1, wherein the providing feedback on the contamination state based on the actual value of the first parameter and the actual value of the second parameter comprises:

developing an expected value for the second parameter based on the actual value of the first parameter;

comparing the expected value for the second parameter to the actual value of the second parameter; and determining a presence of a contaminant based on the comparison or determining an absence of a contaminant based on the comparison.

3. The method according to claim 2, wherein the presence of the contaminant is determined if the difference between the actual value of the second parameter and the expected value for the second parameter is above a threshold, and/or wherein the absence of the contaminant is determined if the difference between the actual value of the second parameter and the expected value for the second parameter is below the threshold.

4. The method according to claim 1, wherein the providing feedback on the contamination state based on the actual value of the first parameter and the actual value of the second parameter comprises:
developing an actual value of a third parameter based on the actual value of the first parameter and the actual value of the second parameter;
comparing the actual value of the third parameter with an expected value for the third parameter; and
determining a presence of a contaminant based on the comparison or determining an absence of a contaminant based on the comparison.

5. The method according to claim 4, wherein the presence of the contaminant is determined if the difference between the actual value of the third parameter and the expected value for the third parameter is above a threshold, and/or wherein the absence of the contaminant is determined if the difference between the actual value of the third parameter and the expected value for the third parameter is below the threshold.

6. The method according to claim 1, further comprising providing reference information, and wherein the providing feedback on the contamination state based on the actual value of the first parameter and the actual value of the second parameter is further based on the reference information.

7. The method according to claim 6, wherein the providing reference information comprises performing reference measurements for one or more known contamination states.

8. The method according to claim 1, wherein the fluid sample is an aqueous liquid or a gas.

9. The method according to claim 1, wherein the fluid sample is a liquid with a refractive index between 1.2 and 1.5, and/or wherein a refractive index of the sensor layer is at least 1.4.

10. The method according to claim 1, wherein the obtaining the time sequence of measurement values includes measuring a luminescence intensity at a plurality of at least three points in time.

11. The method according to claim 1, wherein the first parameter corresponds to a lifetime $\tau$ of the luminescence, and/or wherein the second parameter corresponds to an intensity of the luminescence at a given point in time.

12. The method according to claim 1, wherein the luminophor in the sensor layer is a phosphor with a luminescence lifetime between 1 µs and 1 s; and/or wherein the luminophor in the sensor layer is a phosphor with a luminescence lifetime of at least 10 µs; and/or wherein the luminophor in the sensor layer is a phosphor with a luminescence lifetime up to and including 1 s.

13. The method according to claim 1, wherein the filling the measurement chamber includes bringing the fluid sample in a diffusive equilibrium with the sensor layer, at least with respect to one analyte.

14. The method according to claim 1, wherein the optical sensor is adapted for measuring a partial pressure of a gas fraction in the fluid sample.

15. The method according to according to claim 1, wherein the sensor layer is adapted for a diffusive uptake of an analyte from the fluid sample, and wherein the luminophor in the sensor layer is susceptible to luminescence quenching due to the presence of the analyte in the sensor layer.

16. The method according to claim 1, wherein the optical sensor is adapted to determine a parameter of one or more analytes, wherein the parameter of the one or more analytes is selected from the group of:
pO2, pCO2, pH;
concentrations of electrolytes;
concentrations of metabolic factors; and
concentrations of enzymes.

17. The method according to claim 1, wherein the fluid sample is a liquid selected from the group of blood, diluted or undiluted whole blood, serum, plasma, saliva, urine, cerebrospinal liquid, pleura, synovial liquid, ascites liquid, peritoneal liquid, amniotic liquid, milk, and dialysis liquid samples, or wherein the fluid sample is a medical gas sample selected from the group of respirator gas or expiratory air.

18. A fluid sample analyzer adapted for performing the method of contaminant detection according to claim 1, the fluid sample analyzer comprising the measurement chamber with inlet and outlet ports for feeding and discharging the fluid sample to the measurement chamber and the optical sensor for the detection of a contaminant, the optical sensor comprising the sensor layer with the sensor surface forming the interface to a sample space, stimulus means, detection means, data storage means, and a signal processor,
wherein the sensor layer comprises the luminophor adapted to emit luminescence radiation in response to an excitation stimulus applied to the luminophor;
wherein the stimulus means is arranged for providing the excitation stimulus to the luminophor in the sensor layer;
wherein the detection means is arranged to detect luminescence radiation emitted by the luminophor in response to the excitation stimulus;
wherein the data storage means comprises programmed instructions for:
receiving the time sequence of measurement values for detected luminescence as signals from the optical sensor as an input;
determining the actual value of the first parameter and the actual value of the second parameter, based on the time sequence, wherein one of the first and second parameters is sensitive to the change in refractive index across the interface between the sensor layer and the sample space, and wherein the other one of the first and second parameters is not sensitive to said change in refractive index across the interface between the sensor layer and the sample space;
providing feedback on the contamination state based on the actual value of the first parameter and the actual value of the second parameter,
wherein the signal processor is operable to execute said programmed instructions so as to produce an output indicative of the feedback on the contamination state, and
wherein the optical sensor is arranged such that the sensor surface faces into the sample space defined by the measurement chamber.

19. An optical sensor for the detection of a contaminant, the optical sensor comprising a sensor layer with a sensor surface forming an interface to a sample space, stimulus means, detection means, data storage means, and a signal processor,
wherein the sensor layer comprises a luminophor adapted to emit luminescence radiation in response to an excitation stimulus applied to the luminophor;

wherein the stimulus means is arranged for providing the excitation stimulus to the luminophor in the sensor layer;

wherein the detection means is arranged to detect luminescence radiation emitted by the luminophor in response to the excitation stimulus;

wherein the data storage means comprises programmed instructions for:

receiving a time sequence of measurement values for detected luminescence as signals from the optical sensor as an input;

determining an actual value of a first parameter and an actual value of a second parameter, based on the time sequence, wherein one of the first and second parameters is sensitive to a change in refractive index across the interface between the sensor layer and the sample space, and wherein the other one of the first and second parameters is not sensitive to said change in refractive index across the interface between the sensor layer and the sample space;

providing feedback on a contamination state based on the actual value of the first parameter and the actual value of the second parameter, wherein the signal processor is operable to execute said programmed instructions so as to produce an output indicative of the feedback on the contamination state.

20. A software product that can be loaded to a processor, the processor being configured for communicating with an optical sensor comprising a sensor layer, the sensor layer comprising a sensor surface facing towards a sample space, the sensor layer comprising a luminophor, the processor being further configured for controlling stimulus means adapted for exciting the luminophor, the software product comprising instructions for:

operating stimulus means to apply a stimulus to the luminophor in the sensor layer;

operating the optical sensor to detect luminescence emitted from the luminophor in the sensor layer in response to the stimulus as a function of time;

obtaining a time sequence of measurement values for the detected luminescence;

based on the time sequence, determining an actual value of a first parameter and an actual value of a second parameter, wherein one of the first and second parameters is sensitive to a change in refractive index across the interface between the sensor layer and the measurement chamber, and wherein the other one of the first and second parameters is not sensitive to said change in refractive index across the interface between the sensor layer and the measurement chamber;

providing feedback on a contamination state based on the actual value of the first parameter and the actual value of the second parameter.

* * * * *